US008367061B2

(12) United States Patent
Burioni et al.

(10) Patent No.: US 8,367,061 B2
(45) Date of Patent: Feb. 5, 2013

(54) ANTI-IDIOTYPE MONOCLONAL ANTIBODIES MIMICKING THE HIV GP120 CD4-BINDING (CD4BS)

(75) Inventors: Roberto Burioni, Rimini (IT); Massimo Clementi, Milan (IT)

(73) Assignee: Pomona Ricera S.R.L., Turin (IT)

( * ) Notice: Subject to any disclaimer, the term of this patent is extended or adjusted under 35 U.S.C. 154(b) by 252 days.

(21) Appl. No.: 12/524,816

(22) PCT Filed: Jan. 29, 2008

(86) PCT No.: PCT/IB2008/050307
§ 371 (c)(1),
(2), (4) Date: Jul. 28, 2009

(87) PCT Pub. No.: WO2008/093280
PCT Pub. Date: Aug. 7, 2008

(65) Prior Publication Data
US 2010/0008905 A1    Jan. 14, 2010

(30) Foreign Application Priority Data

Jan. 30, 2007  (IT) .............................. TO2007A0066

(51) Int. Cl.
*A61K 39/395* (2006.01)
*A61K 39/21* (2006.01)
*C12Q 1/70* (2006.01)
*G01N 33/53* (2006.01)
*C07K 16/00* (2006.01)
*B01L 3/00* (2006.01)

(52) U.S. Cl. ....... 424/131.1; 424/208.1; 435/5; 435/7.1; 530/387.1; 422/430

(58) Field of Classification Search .......................... None
See application file for complete search history.

(56) References Cited

U.S. PATENT DOCUMENTS

| 4,946,778 | A | 8/1990 | Ladner et al. |
| 6,057,421 | A | 5/2000 | Muller et al. |
| 2003/0100741 | A1 | 5/2003 | Muller et al. |
| 2004/0224310 | A1 | 11/2004 | McGready |
| 2005/0080240 | A1 | 4/2005 | Kunert et al. |
| 2005/0221298 | A1 | 10/2005 | Muller et al. |

FOREIGN PATENT DOCUMENTS

| EP | 0 621 339 | 10/1994 |
| EP | 0675199 | 10/1995 |
| WO | 84/00687 | 3/1984 |
| WO | 92/15885 | 9/1992 |
| WO | 02/46235 | 6/2002 |
| WO | 02/055560 | 7/2002 |
| WO | 03/064473 | 8/2003 |
| WO | 2007/134327 | 11/2007 |
| WO | 2008/033159 | 3/2008 |
| WO | 2009/037297 | 3/2009 |
| WO | 2009/115972 | 9/2009 |
| WO | 2009/144667 | 12/2009 |

OTHER PUBLICATIONS

Chen, C., et al., 1995, Enhancement and destruction of antibody function by somatic mutation: unequal occurence is controlled by V gene combinatorial associations, EMBO J. 14(12):2784-2794.*
Winkler, K., et al., 2000, Changing the antigen binding specificity by single point mutations of an anti-p24 (HIV-1) antibody, J. Immunol. 165:4505-4514.*
Bansal, G. P., 2007, A summary of the workshop on passive immunization using monoclonal antibodies for HIV/AIDS, held at the National Institute of Allergy and Infectious Diseases, Bethesda, Mar. 10, 2006, Biol. 35:367-371.*
Trkola, A., et al., 2005, Delay of HIV-1 rebound after cessation of antiretroviral therapy through passive transfer of human neutralizing antibodies, Nat. Med. 11(6):615-622.*
Montefiori, D. C., 2005, Neutralizing antibodies take a swipe at HIV in vivo, Nat. Med. 11(6):593-594.*
Haigwood, N. L., 2004, Predictive value of primate models for AIDS, AIDS Rev. 6:187-198.*
Staprans, S. I., and M. B. Feinberg, 2004, The roles of nonhuman primates in the clinical evaluation of candidate AIDS vaccines, Exp. Rev. Vacc. 3(4):55-532.*
PCT International Search Report issued for PCT/IB2009/051068 filed Mar. 16, 2009 in the name of Pomona Biotechnologies.
PCT Written Opinion issued for PCT/IB2009/051068 filed Mar. 16, 2009 in the name of Pomona Biotechnologies.
PCT International Search Report issued for PCT/IB2009/052212 filed May 27, 2009 in the name of Pomona Biotechnologies.
PCT Written Opinion issued for PCT/IB2009/052212 filed May 27, 2009 in the name of Pomona Biotechnologies.
Baca, M., et al., Antibody Humanization Using Monovalent Phage Display, Journal of Biological Chemistry 1997, 272: 10678-10874.
Carter, P., et al., Humanization of an Anti-p185$^{her2}$ Antibody for Human Cancer Therapy, PNAS 1992, 89: 4285-4289.
Cole, S., et al., A Strategy for the Production of Human Monoclonal Antibodies Reactive with Lung Tumor Cell Lines, Cancer Research 1984, 44: 2750-2753.
Molinari, N., et al., The Annual Impact of Seasonal Influenza in the US: Measuring Disease Burden and Costs, Vaccine 2007, 25: 5086-5096.
Rangel-Moreno, J., et al., B Cells Promote Resistance to Heterosubtypic Strains of Influenza via Multiple Mechanisms, The Journal of Immunology 2008, 180: 454-463.

(Continued)

*Primary Examiner* — Jeffrey S. Parkin
(74) *Attorney, Agent, or Firm* — Steinfl & Bruno LLP

(57) ABSTRACT

Novel anti-idiotype monoclonal antibodies are described which are capable of specifically reacting with the idiotype of human anti-gp120 antibodies, of inhibiting the binding between the gp120 antigen and human anti-gp120 antibodies, and of evoking a neutralising anti-gp120 immune response in an animal host to which they are administered. The anti-idiotype antibodies of the invention can be identified based on the amino acid sequences of the variable portions of their light and heavy chains. In addition, a method for obtaining a panel of anti-idiotype monoclonal antibodies, expression vectors and transformed host cells usable in a recombinant DNA procedure in order to generate the aforesaid anti-idiotype monoclonal antibodies, as well as the therapeutic, prophylactic and diagnostic use of such antibodies are disclosed.

13 Claims, 3 Drawing Sheets

OTHER PUBLICATIONS

Figure 1:
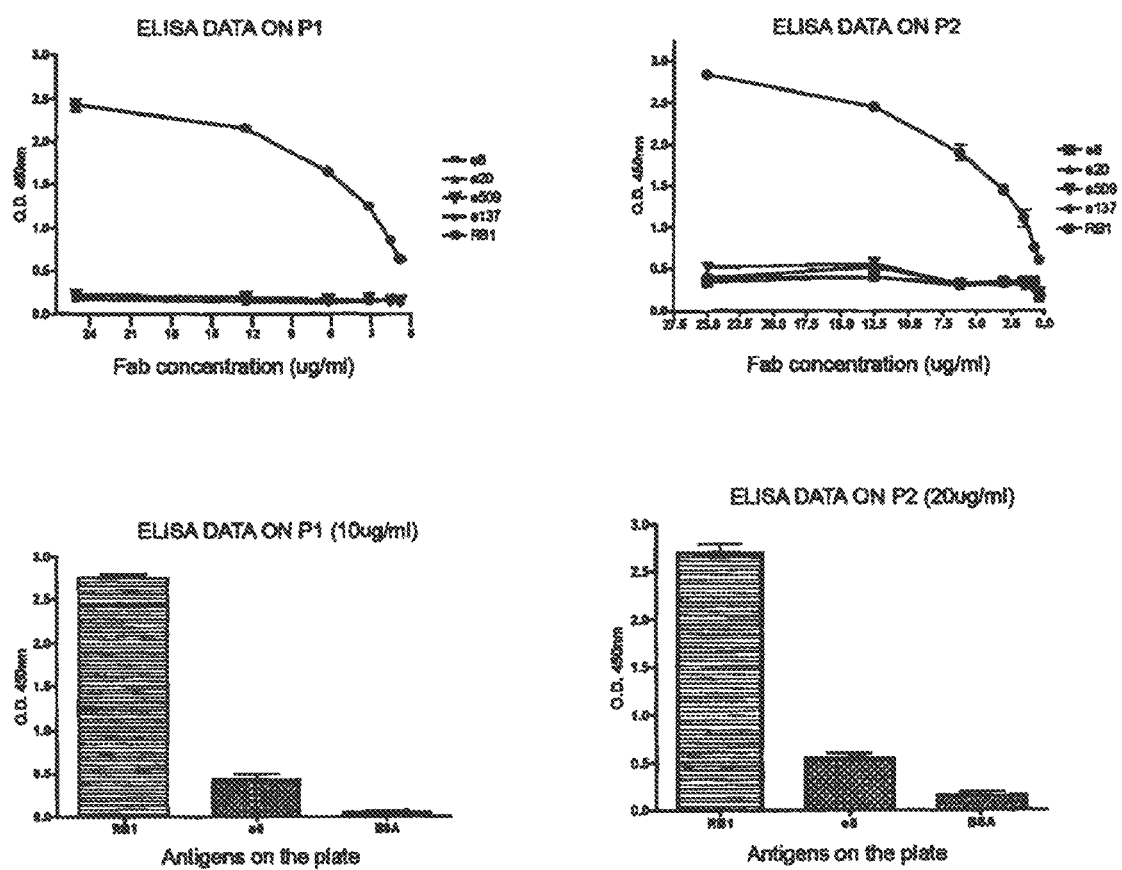

Thompson, W., et al., Mortality Associated with Influenza and Respiratory Syncytial Virus in the United States, JAMA 2003, 289: 179-186.

Ward, E.S., et al., Binding Activities of a Repertoire of Single Immunoglobulin Variable Domains Secreted from *Escherichia coli*, Nature 1989, 341: 544-546.

Austin, F., et al., Antigenic mapping of an Avian H1 Influenza virus haemagglutinin and interrelationships of H1 virus from humans, pigs and birds, Journal Gen. Virol. 1986, 67: 983-992.

Asanuma, H., et al., Influenza PR8 HA-specific fab fragments produced by phage display methods, Biochemical and Biophysical Research Communication 2008, 366: 445-449.

Tkacova, M., et al., Evaluation of monoclonal antibodies for subtyping of currently circulating human type A viruses, Journal of Clinical Microbiology 1997, 35: 1196-1198.

Burioni, R., et al., Dissection of human humoral immune response against Hepatitis C virus E2 glycoprotein by repertoire cloning and generation of recombinant fab fragments, Hepatology 1998, 28: 810-814.

Burioni, R., et al., A vector for the expression of recombinant monoclonal Fab fragments in bacteria, Journal of immunological Methods 1998, 217: 195-199.

Barbass, C., et al., Human primers for fab amplification: Original set, Phage Display Manual, 2004, CSH Press, A1.6-A1.7.

Smirnov, Y. et al., "An epitope shared by the hemagglutinins of H1, H2, H5, and H6 subtypes of influenza A virus." *Acta Virologica* 43(4):237-244 (1999).

Smirnov, Y. et al., "Prevention and treatment of bronchopneumonia in mice caused by mouse-adapted variant of avian H5N2 influenza A virus using a monoclonal antibody against conserved epitope in the HA stem region." *Archives of Virology* 145(8):1733-1741 (2000).

Throsby, M. et al., "Heterosubtypic neutralizing monoclonal antibodies cross-protective against H5N1 and H1N1 recovered from human IgM+ memory B cells." *PLOS One* 3(12):1-15 (2008).

Ziegler, T. et al., "Type- and subtype-specific detection of influenza viruses in clinical specimens by rapid culture assay." *Journal of Clinical Microbiology* 33(2):318-321 (1995).

Nguyen, HH., et al., Heterosubtypic Immunity to Influenza A Virus Infection Requires B Cells but not CD8+ Cytotoxic T Lymphocytes, The Journal of Infectious Diseases 2001, 183: 368-376.

Muller S. et al. "Generation and specificity of monoclonal anti-idiotypic antibodies against human HIV-specific antibodies," Journal of Immunology, vol. 147, No. 3, p. 933-941 (Aug. 1, 1991).

Wang, Haitao et al. "Human monoclonal and polyclonal anti-human immunodeficiency virus-1 antibodies share a common clonotypic specificity," *Eur. J. Immunol. 1992*, 22:1749-1755 (1992).

Humbert, Michael et al. "Mimotopes selected with antibodies from HIV-1-neutralizing long-term nonprogressor plasma," *Eur. J. Immunol. 2007*, 37:501-515 (2007).

Grant, Michael et al. "The anti-idiotypic antibody 1F7 selectively inhibits cytotoxic T cells activated in HIV-1 infection," *Immunology and Cell Biology*, 78, 20-27 (2000).

Muller S. et al. "Stimulation of Antiviral Antibody Response in SHIV-IIIB-Infected Macaques," *Scand. J. Immunol*., 54, 383-395 (2001).

Muller S. et al. "Stimulation of HIV-1-neutralizing antibodies in simian HIV-IIIB-infected macaques," *Proc. Natl. Acad. Sci. USA*, vol. 95 pp. 276-281 (Jan. 1998).

Wang, Q.L. et al. "Identification of an Idiotypic Peptide Recognized by Autoantibodies in Human Immunodeficiency Virus-1-infected Individuals," *The American Society for Clinical Investigation, Inc.*, vol. 96, 775-780 (Aug. 1995).

Boudet, Florence et al. "Anti-Idiotypic Antibodies to the Third Variable Domain of gp120 Induce an Anti-HIV-1 Antibody Response in Mice," *Virology* 200, 176-188 (1994).

Kunert, Renate et al. "Molecular Characterization of Five Neutralizing Anti-HIV Type 1 Antibodies: Identification of Nonconventional D Segments in the Human Monoclonal Antibodies 2G12 and 2F5," *AIDS Research and Human Retroviruses*, vol. 14, No. 13, pp. 1115-1128 (1998).

Kasai, Yasushi et al. "Molecular cloning of murine monoclonal anti-idiotypic Fab," *Journal of Immunological Methods*, 155, 77-89 (1992).

PCT International Search Report for PCT/IB2008/050307 filed on Jan. 29, 2008 in the name of Pomona Biotechnologies LLC.

PCT Written Opinion for PCT/IB2008/050307 filed on Jan. 29, 2008 in the name of Pomona Biotechnologies LLC.

PCT International Preliminary Report on Patentability for PCT/IB2008/050307 filed on Jan. 29, 2008 in the name of Robert Buirioni, et al.

Braibant, M., et al. Antibodies to conserved epitopes of the HIV-1 envelope in sera from long-term non-progressors: prevalence and association with neutralizing activity, AIDS, 2006, 20: 1923-1930.

Bugli, F., et al., Mapping B-Cell Epitopes of Hepatitis C Virus E2 Glycoprotein Using Human Monoclonal Antibodies from Phage Display Libraries, Journal of Virology, Oct. 2001, 75: 9986-9990.

Ward S., et al., Binding activities of a repertoire of single immunoglobulin variable domains secreted from *Escherichia coli*, Nature, 1989, 341: 644-646.

Pantophlet, et al., "GP120: Target for Neutralizing HIV-1 Antibodies", Annual Review Immunology 2006, 24: 739-769.

Hariharan, K., et al., Analysis of the cross-reactive Anti-gp120 antibody population in human immunodeficiency virus-infected asymptomatic individuals, Journal of Virology, 1993, 67: 953-960.

Buironi, R., et al., Dissection of human humoral immune response against hepatitis C virus E2 glycoprotein by repertoire cloning and generation of recombinant fab fragments, Hepatology, 1998, 28: 810-814.

McMicahel, J., HIV Vaccines, Annual Review of Immunology, 2006, 24: 227-255.

Buironi, R., et al., A Vector for the Expression of Recombinant Monoclonal Fab Fragments in Bacteria, Journal of Immunological Methods 1998, 217: 195-199.

Buironi, R. I Treponemi Intestinali Umani, Doctoral Thesis 1993, 1-156.

Geretti AM, editor. Antiretroviral Resistance in Clinical Practice. London: Mediscript; 2006, Chapter 12.

"NIH AIDS Research & Reference Reagent Program, Reagent Information, U87.CD4", https://www.aidsreagent.org/reagentdetail.cfm?t=cell lines&id=20; Jun. 15, 2011, n.p.; Web. Jan. 23, 2012.

"NIH AIDS Research and Reference Reagent Program, About the Program" https://www.aidsreagent.org/about_program.cfm, n.d.; n.p.; Web. Jan. 23, 2012.

Burton, Human primers for fab amplification: original set, Phage Display Manual, A1.6-A1.7, Cold Spring Harbor Laboratory, Cold Spring Harbor, NY 2001.

Burton, Human primers for fab amplification: original set, Phage Display Manual A1.10, Cold Spring Harbor Laboratory, Cold Spring Harbor, NY 2001.

Sui, Jianhua et al., "Structural and functional bases for broad-spectrum neutralization on avian and human influenza A viruses", Nature Structural and Molecular Biolooy 2009, 16: 265-27.

Tarr, A.W. et al., "Determination of the human antibody response to the epitope defined by the hepatitis C virus-neutralizing monoclonal antibody AP33", Journal of General Virology 2007, 88, 2991-3001.

Tarr, A.W. et al., "Characterization of the Hepatitis C Virus E2 Epitope Defined by the Broadly Neutralizing Monoclonal Antibody AP33", Hepatology 2006, 43:3, 592-601.

Perotti, M. et al. "Identification of a Broadly Cross-Reacting and Neutralizing Human Monoclonal Antibody Directed against the Hepatitis C Virus E2 Protein", Journal of Virology 2008, 82:2, 1047-1052.

Johansson, D.X. et al., "Human combinatorial libraries yield rare antibodies that broadly neutralize hepatitis C virus", PNAS 2007, 104:41, 16269-16274.

Burioni, R. et al., "Nonneutralizing Human Antibody Fragments against Hepatitis C Virus E2 Glycoprotein Modulate Neutralization of Binding Activity of Human Recombinant Fabs", Virology 2001, 288, 29-35.

PCT Search Report for International Application PCT/IB2009/055867 filed on Dec. 21, 2009 in the name of Pomona Ricerca S.R.L.
PCT International Preliminary Report on Patentability for International Application PCT/IB2009/055867 filed on Dec. 21, 2009 in the name of Pomona Ricerca S.R.L.
PCT Search Report for International Application PCT/IB2010/052434 filed on Jun. 1, 2010 in the name of Pomona Ricerca S.R.L.

PCT International Preliminary Report on Patentability, International Application PCT/IB2010/052434 filed on Jun. 1, 2010 in the name of Pomona Ricerca S.R.L.
Restriction Requirement mailed on Nov. 14, 2011 for U.S. Appl. No. 13/141,071, filed Jun. 20, 2011 in the name of Roberto Burioni et al.

* cited by examiner

ANTI-IDIOTYPE MONOCLONAL ANTIBODIES MIMICKING THE HIV GP120 CD4-BINDING (CD4BS)

CROSS REFERENCE TO RELATED APPLICATIONS

The present application is the US national stage of International Application PCT/IB2008/050307 filed on Jan. 29, 2008 which, in turn, claims priority to Italian Application TO2007A000066, filed on Jan. 30, 2007.

The present invention relates in general to the immunology field and specifically to anti-idiotype monoclonal antibodies or fragments thereof, which specifically react to human antibodies capable of binding to the human acquired immunodeficiency virus (HIV) gp120 protein and capable of inducing an anti-gp120 response when administered to an animal, including a human being.

BACKGROUND OF THE INVENTION

Over the course of time, the impact of HIV infection has reached worldwide proportions. Throughout the world it is estimated that there are approximately 40 million infected people, with a constantly growing incidence of new infections certified in 5 million new cases per year (UNAIDS-*AIDS Epidemic Update*-2005). The impossibility of carrying out control mechanisms for the infection, or their ineffectiveness, has already determined horrifying pictures in certain areas of the globe. For instance, in certain regions of sub-Saharan Africa (the region of the world most affected by the pandemic) it is estimated that more than 50% of working-age subjects are seropositive, with obvious repercussions on the economies of this area of the world already devastated in any case. But a similar course is also occurring in areas that are experiencing periods of impressive economic growth, such as the Indian subcontinent and South-East Asia. In these areas the number of seropositives is close to 10 million, with an annual exponential increase of new cases (UNAIDS-*AIDS Epidemic Update*-2005).

The antiretroviral therapy, where available, has improved the infected subjects' life expectancy. However it is linked to a series of adverse factors that within a few years could reduce its positive impact. First of all, today's available therapies are not curative; in other words, treated subjects fail to eliminate the virus completely, but remain infected and thus exposed to the risk of developing the severe clinical forms of infection (evident AIDS), and anyway of transmitting the infection to other people. Furthermore, available drugs are burdened with very serious side effects. This causes patients' low compliance with the therapy itself. Low compliance, along with the high molecular adaptability of the virus and other factors, has favoured the onset and spread of completely drug-resistant HIV isolates. Furthermore, the high cost of the therapy makes its use absolutely unlikely on a large scale in the world's depressed areas that, as mentioned above, represent the true explosive reservoir of infection at global level.

Overall, the above described factors make the necessity of working out alternative or, at worst complementary, strategies to the therapy of overriding importance: in the scope of HIV infection control, the development of an effective vaccine approach would certainly have a priority role.

Unfortunately, HIV infection is still nowadays an open challenge and difficult to solve by the scientific community. In fact, traditional vaccine approaches, based on administration of viral particles that are unable to infect but able to stimulate the immune system, have been demonstrated as completely ineffective towards a virus that uses molecular polymorphism, i.e. the ability to mutate in order to escape the immune response, as its own winning weapon (McMichael J., (2006) *Annu. Rev. Immunol.* 24: 227-55).

In the following description, after having briefly illustrated the main immunological mechanisms stimulated by HIV, the various main vaccine strategies followed up to now will be synthetically reviewed, dwelling in particular on the strategy followed in the approach underlying the invention which is the subject of the present patent application, i.e. the attainment and administration of anti-idiotype mimotopes.

The Immune Response Directed Against HIV

The natural history of HIV infection witnesses uncontrolled replication of the virus within early weeks after the infection, with viremia levels that often exceed values of 107 virus particles per ml of plasma within the first 21 days. This first stage is followed by another characterized by a sudden decrease in viremic levels, due to activation of specific response mechanisms, represented by cytotoxic CD8+ T cells and production of neutralising anti-bodies. This stage demonstrates how the immune system, once stimulated, is able to at least partially control the infection. However, the main concern is represented by, as mentioned in the previous section, the hypervariability of certain viral proteins, which enable the virus to overcome the stimulated defenses and thus resume replication in an uncontrolled manner. In the case of HIV infection, the immune system is thus continuously called upon to run after the virus variability: however, the natural history of the infection demonstrates that the immune system results constantly defeated in this chase.

The main object of an effective prophylactic vaccine would then be to present the virus, since the first contact, with an immune response able to block it and thus prevent its uncontrolled propagation in the organism.

Surface HIV proteins (gp120 and gp41), that make target cell infection possible, represent the main targets of the immune response and in particular of humoral-type immune response. Antibodies generated in the course of a natural infection however assure a protection that is limited to the virus that has stimulated such a response. In other words, those very antibodies will not be able to protect the patient who produced them from new viral variants that will develop, and (the most important fact from the vaccine point of view) all the more so would not prove protective for other patients infected by other HIV variants.

The study of HIV-induced antibody response has however evidenced a possible role played by antibody clones with broad neutralising activity against a large panel of virus isolates (Pantophlet R. and Burton D. R., (2006) *Annu. Rev. Immunol.* 24: 739-769). Still, only a few patients are able to produce antibodies with similar features, that will allow them to control the infection for a much longer period, slowing down progression towards evident AIDS (Braibant M. et al., (2006) *AIDS.* 20: 1923-30). These patients are defined by the scientific community as long-term non-progressors (LTNP) and certainly represent an example of anti-HIV immune response to be studied for the development of an effective vaccine.

In the light of the collected data, the scientific community has at this point almost universally recognized that an effective prophylactic or therapeutic vaccine should be able to stimulate an adequate antibody response, analogous to that described in LTNP patients. The main target of a potentially effective humoral response is represented by, as previously mentioned, the two surface glycoproteins (gp120 and gp41) that, in the form of trimers, compose the spikes that enable the virus to bind and penetrate within target cells. However, in particular, conserved key epitopes, and thus common to the different virus isolates, should be detected within these proteins. Laboratory and clinical experimental data have actually proved that the broad neutralising activity response is indeed directed against these epitopes (Braibant M. et al., (2006) *AIDS.* 20: 1923-30). The scientific community unanimously recognizes that the presence of antibodies with similar features at the time of the first contact with the virus most probably would be able to neutralise the infection, attaining what not even the most effective therapeutic protocol has succeeded in obtaining yet, i.e. complete virus clearance (Pantophlet R. and Burton D. R., (2006) *Annu. Rev. Immunol.* 24: 739-769).

Viral Escape Mechanisms

The selective pressure exerted by cellular and humoral immune response against HIV virus has been studied in great depth in literature, although its effects on the progression of immunological deficiency and hence on clinics are not clear. The selective pressure effected by neutralising antibodies is indeed easily observable both in vitro and in vivo since the early infection stages. In fact, the virus escapes through a series of mutations that make the usually generated non-broad range neutralising antibodies useless. Such mutations, that sometimes involve a single amino acid residue, typically implicate the surface glycoproteins and in particular the so-called gp120 protein V (variable) regions. Therefore, it is easily understandable that this key antigen's sequence variability is one of the main reasons for the inability of the antibodies generated in the course of natural infection to completely block the virus. In this context, the molecular reasons of the failure of all "classical" attempts at obtaining a protective response by immunizing subjects with whole virus particles or recombinant gp120 are likewise easily understandable (Pantophlet R. and Burton D. R., (2006) *Annu. Rev. Immunol.* 24: 739-769).

However, HIV defence mechanisms are not limited to the strategy, already effective in itself, of hypervariability. Structural studies of the virus have in fact revealed how HIV exploits its own hypervariable regions in order to hide key epitopes from the immune system too, such as the CD4-binding site and the so-called gp120 coreceptor-binding site, i.e. the protein portions that physically bind the target cell receptor and coreceptors at the time of infection. In other words, the virus would only expose these key regions at the time of direct interaction with the target cell, thus limiting their exposure to the immune system.

Also, HIV has developed another strategy of hiding gp120 most important epitopes: 50% of the molecule is actually covered with carbohydrates, that make the protein surface practically "invisible" to the immune system. In vivo the virus can also modify the positions of this glucidic coating, thus leading to the hypothesis of a dynamic evolution model, the so-called glycan shield. HIV would actually be able to modulate glycosilation, continuously adapting to the kind of immune response that from time to time it has to contrast. Therefore, the ability of escaping the immune response is not a widespread phenomenon, an inherent feature common to all virus particles, but a specific and continuous adaptation to the neutralising antibody response that is stimulated each time.

gp120 as a Potential Vaccine Target

As disclosed in the two previous sections, gp120 represents the main target of HIV virus-neutralising immune response. However, in the previous sections, the molecular reasons why classical vaccine approaches, even though contemplating the use of an antigen so important to the virus, did not lead to positive results have been pointed out. In particular, the use of inactivated whole virus particles, or of gp120 recombinant monomeric forms, leads to stimulation of an immune response merely limited to the virus used in the vaccine protocol, or from which the recombinant protein had been obtained. For instance, the stimulated response turned out to be limited to HIV isolates adapted in laboratory to grow on immortalized T cell line cultures. Instead, no antiviral effect was seen against "primary" virus isolates, i.e. isolates directly derived from infected patients.

The failure of these approaches has led to investigation of possible alternative routes that will be briefly disclosed in this section of the specification, and can be synthetically divided into two groups.

a) Development of gp120 Trimeric Preparations which Represent the Protein Structure Displayed on HIV Spikes Better.

This approach relies on administration of gp120, no longer in monomeric form but in heterotrimeric form, in association with the other viral surface glycoprotein, the gp41 protein. The principle at the root of this strategy is based on the observation of the different anti-genic features of monomeric gp120 compared to the trimeric forms (Pantophlet R. and Burton D. R., (2006) *Annu. Rev. Immunol.* 24: 739-769). However, the first data collected from approaches regarding this strategy have revealed a series of problems tightly connected with each other, both from the technical point of view and from the point of view regarding the effectiveness of the approach itself. From the technical viewpoint, the main obstacle to be overcome consists indeed in the ability of obtaining stable heterotrimeric forms that are best able to mime the organisation of the viral envelope spikes. On HIV surface, in fact, gp120-gp41 interactions are mediated by non-covalent interactions essential in order to give the overall structure of the spike the indispensable structural adaptability that characterizes its function. In laboratory, it has proved particularly difficult to obtain such molecules, which on one hand should be stable enough not to dissociate into single monomers, and on the other hand should however be able to display critical portions of the proteins, and particularly of gp120. It has therefore been necessary to adopt a series of technical stratagems in order to stabilize the trimers (mutation into the original polyprotein cleavage sites, insertion of cysteine residues into unimportant portions of the structure), or to display them onto structures as similar as possible to the viral envelope (inclusion into proteoliposomes, expression on virus-like particles). However, none of the approaches followed have allowed for completely solving the trimer stabilisation and purification problems, nor have they led to definitely superior results compared to those obtained with monomeric forms of gp120, in terms of efficacy and especially of the extent of the neutralising activity. The results obtained with approaches contemplating the use of gp120 recombinant forms mutated in order to make key portions of the protein more available to the immune system were similarly unsatisfactory.

b) Development of Innovative Epitope-Based Vaccines i.e. Based on Exposure to the Immune System of Conserved, Therefore Potentially Protective, Portions of gp120.

This group is connected with the anti-idiotype mimotope strategy, on which the invention illustrated in the present patent application is also based.

The main problem with all the above illustrated strategies concerns the inability to stimulate, in addition to a type-specific neutralising response, a broad range neutralising response. The so-called epitope-based approaches must be considered within the sphere of the attempts to reduce the type-specific response and enhance the cross-neutralising one.

To better understand the strategies connected with this group, it is useful to make a brief reference to the gp120 antigen structure. Based on comparative sequence analysis, the study of gp120 reveals, as regards the glycoprotein, 5 conserved (C1-C5) and 5 variable (V1-V5) segments. Further studies have demonstrated that the C1 and C5 regions are probably engaged in the contact with gp41, as it has been evidenced that antibodies directed against this region only recognize monomeric forms of gp120, not the trimeric ones. Instead, certain portions of the C2, C3 and C4 regions possibly form a hidden and relatively hydrophobic nucleus within the gp120 molecule, probably involved in CD4 receptor recognition. Unlike conserved regions, the variable regions (particularly V1, V2 and V3) are well exposed and accessible on the protein.

The epitope-based approaches in fact attempt to exploit gp120 structural features in order to obtain molecules that are able to target the immune response exclusively, or predominantly, to its key epitopes. In this context, one strategy has been to use gp120 monomers, from which the V1, V2 and V3 regions had been removed, in order to expose the conserved CD4-binding portions to the immune system. A similar approach has not yet given satisfactory results, also because the removal of such large portions from the protein has inevitable effects on its whole conformation and hence on the CD4-binding portion that might lose its own distinctive features.

Another possible strategy is to exploit, to the immune system's advantage, one of the HIV escape mechanisms previously disclosed, i.e. hyperglycosylation of gp120 portions. In this connection, artificially glycosylated gp120s have been obtained in laboratory, in order to hide non-protective sites and target the response exclusively to the protein's important portions. However, the results obtained with this approach have been unsatisfactory, in as much as this strategy, although leading to a reduction in the immune response directed against non-conserved portions of the molecule, has not been able to cause an extensive response to gp120 crucial portions.

At this point, it is useful to recall that, in some rare cases and in very low titres, in the course of certain natural infections, antibodies capable of neutralising a broad range of viral isolates are generated. Such antibodies (extremely rare and precious from the scientific point of view) thus represent an ideal template for an extremely targeted epitope-based approach. Exploiting the idiotype of these molecules (i.e. the antibody portion that specifically recognizes and binds the antigen), it is possible, by using a reverse vaccinology approach, to obtain other (anti-idiotype) antibody molecules which are specifically directed against the idiotype of broad range neutralising antibodies, and thus able to mime the key epitopes that they recognize. In other words, well designed anti-idiotype antibodies may represent an artificial antigen unrivalled in laboratory, as they are able to expose just the neutralising antibody-recognized key epitope to the immune system.

The analysis of prior scientific and patent literature has allowed for pointing out that anti-idiotype-based strategies have already been applied to HIV infection.

However, as far as the inventors know, the majority of prior literature relates to anti-idiotype antibodies obtained using, as the cloning template, non-human derived, especially mouse-derived, antibody molecules, i.e. antibodies obtained immunizing laboratory mice with recombinant gp120. As it has been many times scientifically demonstrated that one identical epitope may be able to stimulate a specific antibody response in an experimental animal but not in human beings, the choice of using non-human derived polyclonal preparations or monoclonal antibodies as the template for obtaining anti-idiotype antibodies makes the attainment of anti-idiotype antibodies useful for vaccine purposes in man uncertain; i.e. it is uncertain that they would be capable of effectively miming fundamental gp120 antigen portions recognized by the human immune system and of accordingly being able to stimulate an effective immune response in human beings.

Human-Derived Template Antibodies

However, a few prior documents describe human monoclonal antibodies with neutralising activity, which in some cases are proposed as the template for obtaining of anti-idiotype molecules. The majority of such prior documents, however, do not describe in practical terms the production of anti-idiotype molecules, nor their properties and applications.

The inventors are acquainted with only one prior patent document in which the achievement of anti-idiotype antibodies starting from human-derived template antibodies is concretely disclosed. It is International Patent Application WO 92/15885, published on Sep. 17, 1992. This patent application discloses a method for selection of anti-idiotype monoclonal antibodies useful for vaccine purposes for the prophylactic or therapeutic treatment of HIV infections. In brief, this method contemplates the attainment of anti-idiotype monoclonal antibodies (G1-Ab2s) using as the template a polyclonal preparation of whole anti-gp120 human Igs (Ab1s), the subsequent selection of a subset of anti-idiotype monoclonal antibodies (G2-Ab2s) characterized by the ability to react with in vitro multiple HIV strain-neutralising anti-gp120 antibodies, and the selection of a further subset of anti-idiotype monoclonal antibodies (G3-Ab2s) capable of generating, in a primate host, an anti-anti-idiotype antibody (Ab3) response, which antibodies react with the gp120 antigen and have HIV neutralising properties.

The procedure described in the WO 92/15885 application shows several disadvantages. First of all, by using whole immunoglobulins as the template, a panel of anti-immunoglobulin monoclonal antibodies are obtained which are mostly directed towards useless portions of the template immunoglobulins, i.e. the portions outside the idiotype, and which for the most part are therefore not true anti-idiotypes. Furthermore, the neutralising response achieved in primates disclosed in this patent application is weak and requires prior purification of the antibodies used in the immunization. It can thus be concluded that the antibodies obtained with the WO 92/15885 method, besides not being sufficiently specific to the useful portion of the anti-gp120 immunoglobulins (the idiotype), are not able to evoke a strong neutralising immune response (low antibody titres) and thus are not particularly promising as vaccines.

OBJECT OF THE INVENTION

The object of the present invention is to deal with the above illustrated problems of the prior art.

More particularly, one object of the invention is to provide anti-immunoglobulin monoclonal antibodies, or antibody fragments thereof, that are able to immunologically bind to the idiotype of human anti-HIV gp120 antibodies and which can therefore be defined as "anti-idiotype antibodies".

Another object of the invention is to provide anti-idiotype monoclonal antibodies, as hereinabove defined, or antibody fragments thereof, that are able to inhibit the immunological binding between the gp120 antigen and human anti-gp120 antibodies.

Another object of the invention is to provide anti-idiotype monoclonal antibodies, as hereinabove defined, or fragments thereof, that are able to evoke a rapid and strong anti-antiidiotype antibody immune response directed against HIV, when administered to an animal, including a human being.

Another object of the invention is to provide a method for the preparation of anti-idiotype monoclonal antibodies, as hereinabove defined, or fragments thereof, allowing for obtaining a panel of monoclonal antibodies that are specifically directed towards the useful portion of the human anti-gp120 immunoglobulins used as the template, i.e. their idiotype, and which are able to neutralise the HIV virus.

DESCRIPTION OF THE INVENTION

These and other objects are achieved by the anti-idiotype antibodies, their nucleotide and amino acid sequences and the preparation method thereof, as defined in the appended claims. The claims form an integral part of the description.

More particularly, the invention relates to a method for the preparation of suitable anti-idiotype monoclonal antibodies for the prophylactic or therapeutic treatment of HIV infection or diseases related thereto, which comprises a first step wherein a preparation of human polyclonal antibodies directed towards the HIV gp120 antigen (and therefore further referred to as "anti-gp120 antibodies") is provided, which preparation will subsequently be used as the template for the preparation of anti-idiotype antibodies.

It is important that the preparation of human polyclonal anti-gp120 antibodies to be subsequently used as the template is pre-selected for its broad range neutralising activity against HIV. The pre-selection is preferably carried out by choosing, as the antibody source, sera from HIV-positive patients clinically characterized by a slow progression of the disease (long-term non-progressors). Such patients are chosen by following the extremely stringent clinical-virological criteria illustrated in the experimental section of the description. The observance of such criteria allows for obtaining serum samples with a considerable broad range HIV neutralising activity. The verification of the neutralising activity can be carried out by using methods and techniques known per se, which the person skilled in the art is able to apply to the specific case without the exercise of any inventive activity and without undue experimentation.

Preferably, the human polyclonal anti-gp120 antibodies used as the template are purified anti-gp120 immunoglobulins G (IgG). The purification is preferably effected by (immuno) affinity chromatography procedures, for example, by using G protein-containing sepharose columns for IgG purification and gp120-containing columns for the purification of specifically HIV gp120 antigen-directed antibodies.

Another preferred feature of the human polyclonal anti-gp120 antibodies used as the template is that they are in the form of Fab fragments. Therefore, in a preferred embodiment of the method, the purified anti-gp120 IgGs, with a broad range HIV-neutralising activity, are provided as Fab fragments. Such anti-gp120 Fab fragments having a neutralising activity will be further referred to as "RB1Fabs".

In the second step of the method, the RB1Fabs are used as the template for generating anti-immunoglobulin monoclonal antibodies that are directed towards the idiotype of the same RB1Fabs used as the template. Such anti-immunoglobulin antibodies are further referred to as "anti-idiotype antibodies".

The expressions "directed towards" and "directed against" are used to indicate that the antibodies at issue are able to react with, i.e. to immunologically bind to, the indicated antigen.

As known, the Fab fragments are antibody fragments capable of binding the antigen, obtainable by digestion of whole immunoglobulins with the papain enzyme. More particularly, a Fab fragment consists of an intact light chain associated with a VH-Cγ1 fragment of a heavy chain. By digestion of a whole IgG with the papain enzyme, two identical Fab fragments are obtained.

Within the scope of the inventive method, the use of Fab fragments as the template for generating anti-immunoglobulin monoclonal antibodies advantageously allows for obtaining a panel of antibodies that are more specifically directed towards the useful portion of the immunoglobulins used as the template, i.e. their idiotype. Therefore, such antibodies are referred to as "anti-idiotypes". The term "idiotype" refers to the totality of the hyper-variable regions of the variable domain of an immunoglobulin, which is to say those structures that characterize a homogeneous population of antibody molecules, such as for example the proteins of a myeloma or a monoclonal antibody, and thus allow for distinguishing between one homogeneous population of antibody molecules and another homogeneous population (for instance, between one monoclonal antibody and another).

Any conventional technology for the preparation of monoclonal antibodies, for example, but without limitation, the hybridoma technique, the phage display technique, the yeast display technique, the ribosome display technique, can be used to obtain the panel of anti-idiotype monoclonal antibodies. Preferably, the anti-idiotype monoclonal antibodies obtained in this step are mouse antibodies, generated by the hybridoma technique by immunizing mice with the RB1Fabs.

Finally, in the third step of the method, the panel of anti-idiotype monoclonal antibodies obtained in the second step is screened to select a subset of antibodies with the ability to inhibit the binding of gp120 to human anti-gp120 antibodies, preferably to the RB1Fabs used as the template. This allows for ascertainment that the anti-idiotypes obtained with the inventive method are true mimotopes, i.e. anti-idiotype antibodies capable of immunologically mimicking the gp120 antigen. The screening can be carried out by any suitable known method for such purpose, for example by ELISA, as described in the following experimental section.

The scope of the invention also includes a panel of anti-idiotype monoclonal antibodies, preferably mouse antibodies, characterized by being specifically directed against the idiotype of human anti-gp120 antibodies and by being able to inhibit the binding between gp120 and human anti-gp120 antibodies. Such a panel of anti-idiotype monoclonal antibodies is obtainable by the method of the invention.

The term "panel of anti-idiotype antibodies" is used to indicate the totality of the different populations of anti-immunoglobulin monoclonal antibodies that are generated with the inventive preparation method. Thanks to the specific preparation method used, the various populations of anti-immunoglobulin monoclonal antibodies obtained, although differing from one another precisely in the structure of the antigen-binding regions, all share a common feature, i.e. they are directed towards the idiotype of the RB1Fabs used as the template, and thus can be defined as populations of anti-idiotype monoclonal antibodies.

From the above explanation, it is thus evident that, within the scope of the present description, the term "anti-immunoglobulin antibody" is not synonymous with the term "anti-idiotype antibody". An anti-immunoglobulin antibody generically is an antibody obtained by immunizing an animal with an immunoglobulin, which in this case acts as the antigen. The anti-immunoglobulin antibody can be directed towards any immunoglobulin region used as the antigen, including, for instance, the Ig constant region or other conserved portions. Instead, an anti-idiotype antibody is an anti-immunoglobulin antibody specifically directed towards the idiotype of the immunoglobulin used as the antigen. Therefore, the category of the anti-idiotype antibodies is more specific than that of the anti-immunoglobulin antibodies.

The experimental section of the present patent application illustrates in detail the method for the preparation of the anti-idiotype monoclonal antibodies of the invention and the immunological features that make some of the obtained antibodies particularly effective in vaccine (therapeutic or prophylactic) applications against HIV infection or diseases related thereto. The attainment of anti-idiotype monoclonal antibodies in the form of Fab fragments is specifically illustrated in the experimental section. Also, two specific anti-idiotype Fabs (designated as P1 and P2) are described, which were obtained by molecular biology techniques starting from hybridomas, and identified by the amino acid and nucleotide sequences of the variable portions of their heavy and light chains. Such sequences are provided in the specification section entitled "Sequence listing".

Obviously, the anti-idiotype antibodies of the invention, including P1 and P2, can be prepared and used in forms other than the Fabs, for instance as whole immunoglobulins, or else in the form of other antibody fragment types (for example $F(ab')_2$ fragments or anti-body fragments smaller than the Fabs) or even as peptides having the same immunological properties as the Fabs of the invention.

For example, single chain antibodies can be constructed according to the method described in U.S. Pat. No. 4,946,778 by Ladner et al., incorporated as reference herein. Single chain antibodies comprise the light and heavy chain variable regions connected through a flexible linker. The antibody fragment designated as single domain antibody is even smaller than the single chain antibody, as it is comprised of a single isolated VH domain. Techniques for obtaining single domain antibodies having at least in part the same binding ability as the whole antibody are known in the prior art. For example, Ward, et al., in "Binding Activities of a Repertoire of Single Immunoglobulin Variable Domains Secreted from *Escheria coli*," Nature 341:644-646, describe a screening method for attaining the variable region of an antibody's heavy chain (VH single domain antibody) with sufficient affinity to the target epitope so that it will bind to it in an isolated form.

In the following description, the term "anti-idiotype antibody" will therefore be used to refer to all the above mentioned anti-idiotype antibody embodiments, i.e. whole immunoglobulins, Fab fragments or other antibody fragment types, single chain antibodies, single domain antibodies, etc.

The anti-idiotype antibodies of the invention can be generated and used in a free form or in a carrier-conjugated form. A carrier is any molecule capable of conjugating with an anti-body and making it immunogenic or increasing its immunogenicity.

Non-limiting examples of carriers are proteins such as KLH (keyhole limpet hemocyanin), edestin, thyroglobulin, albumins such as bovine serum albumin (BSA) or human serum albumin (HSA), erythrocytes such as sheep erythrocytes (SRBC), tetanus anatoxin, cholera anatoxin, polyamino acids such as poly(D-lysine:D-glutamic acid) and the like. In order to facilitate the binding of the anti-idiotype to the carrier, the anti-idiotype C-terminus or N-terminus may be modified, for example, by insertion of additional amino acid residues, for instance one or more cysteine residues that are able to form disulfide bridges.

Because of their properties, which will be shown in detail in the experimental section, the anti-idiotype antibodies of the invention are particularly suited for use in therapeutic and/or diagnostic applications, particularly in the manufacture of a medicament for the prophylactic or therapeutic treatment of HIV infection or diseases related thereto, and in methods for the detection of anti-HIV gp120 antibodies in biological samples.

As previously mentioned, the invention also provides the amino acid and nucleotide sequences of the heavy and light chain variable regions of two specific anti-idiotype Fabs of the invention, designated as P1 and P2 respectively. As described in detail in the experimental section, the P1 and P2 Fabs have been obtained by means of molecular biology techniques starting from two hybridomas, designated as Mab1 and Mab2, which were able to produce anti-idiotype monoclonal antibodies capable of inhibiting the immunologic binding between gp120 and the RB1Fabs. The exact procedures used to generate the P1 and P2 Fabs of the invention are disclosed in detail in the experimental section. In general terms, the mRNA of the genes encoding for the light and heavy chain variable regions of the monoclonal produced by the Mab1 hybridoma was cloned into an expression vector known per se, designated as RBCaf, and the recombinant construct thus obtained was transformed into *E. coli* strain XL1Blue cells that had been made competent. The same procedure was applied to the monoclonal antibody produced by the Mab2 hybridoma. About 40 recombinant bacterium clones were obtained for each monoclonal antibody. The recombinant bacterium clones were then selected according to their ability to generate mouse Fabs capable of binding the purified RB1Fabs. Two clones were selected in this way, one for each monoclonal, designated as Pomona1 (P1) and Pomona2 (P2), respectively. The amino acid and nucleotide sequences of the heavy and light chain variable regions of the mouse P1 and P2 Fabs have been obtained. Such sequences are reported in the section entitled "Sequence listing".

The mouse P1 and P2 Fabs resulted as advantageously positive, not only for their ability to inhibit the gp120-RB1Fab binding, but also for their ability to stimulate a specific anti-gp120 immune response in animal models other than mice, for instance in rabbits. The immunisation experiments described in the experimental section of the patent application show that these Fabs are able to evoke a rapid and strong specific anti-gp120 immune response, also evident at high serum dilutions (1:1600). It has also been possible to verify that the anti-gp120 antibodies evoked in rabbit in response to immunisation with the P1 and P2 Fabs of the invention display a high HIV-neutralising ability. The obtained data indicate that the P1 and P2 molecules of the invention are particularly useful in vaccine applications, especially for the prophylactic and therapeutic treatment of HIV infection or diseases related thereto.

Not only are such properties predicted on the basis of the observation that the ability of the inventive antibodies to evoke a robust antiviral immune response (without using the virus) has been ascertained in an animal model phylogenetically very distant from man, such as the rabbit, but they have also been experimentally verified by neutralising activity evaluation assays of sera from rabbits immunized with the anti-idiotype monoclonal antibodies of the invention. The results of such neutralisation experiments, which have been performed using a human glyoma cell line, are illustrated in the following experimental section.

Thus, an immunogenic composition comprising an immunologically effective amount of at least one anti-idiotype antibody of the invention (preferably a P1 or P2 molecule) and a pharmaceutically acceptable carrier and/or diluent is also included in the scope of the invention. An immunologically effective amount of at least one anti-idiotype antibody of the invention is an amount that is able to induce an anti-gp120 immune response in an animal host to which it is administered, including a human being.

Optionally, the immunogenic composition can further comprise one or more adjuvants. An adjuvant is a compound having a non-specific stimulation activity on the immune system. Non-limiting examples of adjuvants are complete Freund's adjuvant, incomplete Freund's adjuvant, vitamin E, non-ionic block polymers, muramyl peptides, immunostimulant complexes, saponins, mineral oils, vegetable oils, Carbopol, thermolabile *E. coli* toxin (LT), cholera toxin (CT), aluminium hydroxide, aluminium phosphate or aluminium oxide, etc.

Other non-limiting examples of useful pharmaceutically acceptable carriers or diluents for the immunogenic composition of the invention include stabilizers such as SPGA, carbohydrates (for example, sorbitol, mannitol, starch, sucrose, glucose, dextran), proteins such as albumin or casein, protein-containing agents such as bovine serum or skimmed milk, and buffers (for example phosphate buffer).

As will be described in detail in the following experimental section, it has been ascertained that the results achievable by immunization of test animals (for example, rabbits) with the anti-idiotype molecules of the invention can be further improved (in terms of the anti-gp120 immune response intensity, see FIG. 3) by subjecting the animals to a particular immunization regime, which contemplates the simultaneous, separate or sequential administration of the anti-idiotype antibodies of the invention (preferably P1 or P2) and the gp120 antigen or other naturally occurring or artificial antigens.

Therefore, a kit of parts comprising an anti-idiotype antibody of the invention, preferably P1 or P2, and the HIV gp120 antigen or other naturally occurring or artificial antigens, as a combined preparation for the simultaneous, separate or sequential administration in a therapeutic or prophylactic immunization regime against HIV, is also included in the scope of the present invention.

Finally, given their proven ability to specifically react with anti-HIV gp120 antibodies, the anti-idiotype antibodies of the invention, preferably P1 and P2, can be used as diagnostic reagents in an in vitro method for detection of anti-gp120 antibodies and/or antibody subpopulations in a biological sample, such as for example a sample of serum, plasma, blood or any other suitable biological material derived from an animal, including a human being, for example a patient infected or suspected of being infected by HIV.

Experimental Section

Obtaining Human IgGs from HIV Virus-Neutralising Sera

Human IgGs were purified from sera of HIV-positive patients clinically characterized by a slow progression of the disease (long-term non-progressors).

These patients were chosen by following the most stringent clinical-virological criteria in the definition of long-term non-progressors. All the selected patients in fact were characterized by the following parameters:

- HIV-seropositive for at least 8 years;
- CD4+ T lymphocyte levels exceeding 600 cells/P1 for at least 5 years (this is an extremely important parameter for the evaluation of the chosen subjects' immunological status, not only at the time of the study, but also during a long period of time before the study);
- no HIV-related clinical signs for at least 5 years (this is an extremely important indication of control of infection over time).

By following these parameters it has been possible to obtain over time (with obvious difficulties given the strictness of the proposed criteria) serum samples with a surprisingly broad range neutralising activity, and thus optimal for the continuation of the study.

Furthermore, not all of the selected patients' serum samples have been used as the polyclonal preparation template to obtain anti-idiotypes: only sera capable of significantly inhibiting a broad panel of HIV isolates have been chosen for the continuation of the study.

Serum aliquots from these patients were assessed for their HIV-1-neutralising ability.

Briefly, for the virus neutralisation, a reference lymphotropic virus strain (HIV-1IIIB) (Advanced Biotechnologies Inc.-ABI) was first titrated by Karber's method (Oxford University Press, Virus Culture-A Practical Approach, ed. A. J. Cann, p. 84) on a HTLV-1-transformed human cell line (C8166-ECACC #88051601), using 6 replicas for each virus dilution (range: 1:10 to 1:16000), thereby obtaining a virus titre expressed as $TCID_{50}$ (i.e. the dose capable of determining a cytopathic effect in 50% of the infected cells). In the neutralisation tests, 100 $TCID_{50}$ were thus preincubated with stepwise dilutions of the chosen sera, assessing the ability of the latter to inhibit C8166 cell infection by the virus. To that end, culture supernatants were taken at days 3, 7 and 10 post-preincubation in order to measure the viral p24 (Vidas® HIV Duo Ultra, Biomerieux).

Sera with higher neutralising activities were selected, and all of the aliquots were combined. Purification of the IgGs from serum was carried out by immunoaffinity chromatography. In short, the pool of neutralising sera was diluted with 3 volumes of PBS (phosphate buffered saline: NaCl 8 mg/ml; KCl 0.2 mg/ml; $Na_2HPO_4$ 1.44 mg/ml; $KH_2PO_4$ 0.24 mg/ml) and filtered through 0.45 μm filters (Millipore Corporation; Bedford, Mass.). The filtrate was then passed through a protein G-containing sepharose column (Gammabind Sepharose™, GE Healthcare Life Sciences, UK). Subsequent to one washing of the column with 10 volumes of PBS, the bound IgG component was eluted with 10 volumes of 0.1 M citric acid, pH 3, and quickly neutralised with a basic solution (1.5 M Tris-Base). The various obtained fractions were then read in a spectrophotometer (O.D. 280 nm) in order to assess the amount of IgG obtained.

Purification of Anti-HIV gp120 Antibodies

Antibodies directed against HIV gp120 glycoprotein were purified by modifications of a technique already described (Hariharan et al, 1993). Briefly, 700 μg of a recombinant type IIIB gp120 glycoprotein (ImmunoDiagnostics Inc., Woburn, Mass.) were coupled through covalent binding to CNBr-activated Sepharose 4B (CNBr-activated Sepharose™ 4B, GE Healthcare Life Sciences, UK). The aforesaid amount of antigen dissolved into 4 ml of coupling buffer (100 mM $NaHCO_3$; 500 mM NaCl; adjusted to pH 8.2 with HCl) was added to 4 ml of 50%-reconstituted resin, after a washing with 1 mM HCl. The mixture was subjected to rotary mixing overnight at 4° C., and the excess non-bound antigen was washed with an excess of coupling buffer. The resin was then transferred into a 10 ml syringe and washed with ten volumes of 10 mM Tris, pH 7.5. 10 volumes of 100 mM glycine (pH 2.5) were then applied to the column, followed by 10 volumes of 10 mM Tris (pH 8.8) and 10 volumes of 100 mM triethylamine (pH 11.2), and finally the column was washed with 10 mM Tris (pH 7.5) until the pH reached 7.5.

The patients' antibodies, diluted 1:3 into 10 mM Tris (pH 7.5), were slowly passed 7 times onto the resin-containing column at 4° C. The column was then washed with 10 volumes of 10 mM Tris (pH 7.5) and the antibodies were finally eluted with 100 mM glycine (pH 2.5), and immediately neutralised. The fractions were analysed for their reactivity towards gp120 by ELISA. In particular, each well was coated with 100 ng of antigen resuspended into 25 ml of PBS, and subsequently the plates were incubated overnight at 4° C. Similarly, some wells were coated with a control antigen, bovine serum albumin (BSA-#A7030-Sigma, St. Louis, Mo.). The excess antigen not bound to the plate was then removed by a series of washings with distilled water. The plates were blocked with PBS/1% BSA, and incubated for 1 hour at 37° C. Stepwise dilutions (from 1:100 to 1:6400) of each of the purified fractions as described were then added and allowed to incubate with the antigens for 2 hours at 37° C. After a round of 10 washings with PBS/0.05% Tween 20, 40 µl of a 1:700 dilution in PBS/1% BSA of a horseradish peroxidase-conjugated goat polyclonal antibody solution (Sigma, St. Louis, Mo.), directed against the Fc portion of human IgGs, were added to each well. After a 1 hour incubation at 37° C., another 10 washes with PBS-Tween were carried out. The enzyme substrate (OPD-o-phenylenediamine-Sigma) was then added to the wells, and the signal was detected by spectrophotometric reading at 450 nm O.D., care being taken to compare the gp120 values with the BSA values.

The fractions containing anti-gp120 antibodies were combined in a single preparation and concentrated by ultrafiltration.

The absence of contaminating antibodies was demonstrated by analyzing the purified anti-bodies for their reactivity towards antigens against which antibodies were present in patients' serum before the preparation (Herpes Simplex Virus and Rubella Virus antigens). To that end, Vero cells (ATCC # CCL-81) had been infected with the two viruses (ATCC # VR-733; ATCC # VR-553). After a 6 day incubation at 37° C., the infected cells (and non-infected Vero cells as a negative control) were collected. The cell pellets were then resuspended into 250 µl of lysis buffer (50 mM Tris-HCl pH 8, 150 mM NaCl; 0.02% Sodium Azide; 0.5% Triton-X), incubated for 20 minutes in ice and centrifuged at 12000 g for 2 minutes at 4° C. The protein concentration in the supernatant was then calculated by using a commercially available kit (BCATM Protein Assay Kit-Pierce, Rockford, Ill.). 300 ng of protein extract were then used to coat ELISA plate wells, according to the protocol previously described for gp120.

Production of Fab Fragments

Fab fragments from the purified anti-gp120 IgGs were produced by using the Pierce ImmunoPure Fab Preparation Kit (Pierce, Rockford, Ill.) according to the instructions provided by the manufacturer. The human Fabs obtained by this experiment (designated as RB1Fabs) were used to immunize mice and for some ELISA assays described further below.

Production of Mouse Anti-Idiotype Monoclonal Antibodies (Mabs)

Female 4-6 weeks old Balb/c mice (Charles River Corporate, Wilmington, Mass.) were immunized by a weekly intraperitoneal injection repeated three times with 0.5 ml PBS containing about 50 µg purified human Fabs (RB1 Fabs), together with an equal volume of incomplete Freund's adjuvant (Gibco). These 3 administrations were followed by another 3, again weekly via the intraperitoneal route, but without the incomplete adjuvant. Before the start of the protocol, and after this immunization schedule, blood was drawn and each animal's antibody response to Fabs derived from purified IgGs of HIV-seronegative patients' sera was assessed by ELISA. Briefly, the assay was carried out as described for the previous ELISAs, by coating the wells with 300 ng of Fabs. Stepwise dilutions (from 1:100 to 1:6400) were then prepared from each animal's pre-immune serum and from the serum drawn after the immunization protocol. Mouse antibodies bound to the different preparations were then detected by a polyclonal preparation of goat antibodies (Sigma, St. Louis, Mo.) directed against the Fc portion of the mouse antibodies. In the event of a satisfying response (O.D. 450 of the immune serum 1:1600 dilution at least >1.5 over the value obtained with the pre-immune serum), a final antigen inoculation was then carried out 3 days before the sacrifice of the animals for the fusion.

Production of Mouse Monoclonal Antibodies

Production of mouse monoclonal antibodies was carried out by using the already described methodology (R. Burioni, doctoral thesis, 1993) with a few modifications.

Briefly, cells derived from a mouse NS-1 myeloma cell line (ECACC #85011427) were used as the fusion partner. The cells as well as the hybridomas originated from them were cultured in RPMI-1640 medium (Gibco) supplemented with 20% complement-inactivated bovine fetal serum (Flow). Two media were used for the fusion. The first one, called fusion medium, was prepared with 5 ml of EMEM medium (Invitrogen), 0.75 ml of Dimethylsulfoxide and 4.75 ml of PEG1540. Instead, HAT and HT selective media were prepared with 375.5 ml of RPMI-1640 medium, 100 ml of complement-inactivated bovine fetal serum, 13.5 ml of 7% sodium bicarbonate, and 5 ml of a 100×HAT solution (Ipoxantine 1.36 mg/ml, Thymidine 0.388 mg/ml, Aminopterin—not present in the HT medium—0.019 mg/ml). Penicillin (100 mIU/ml), Streptomycin (100 µg/ml), L-glutamine (2 mM final concentration) and Amphotericin B (100 µg/ml) were also added to the media.

Three days after the last inoculation contemplated by the immunization schedule, the mice were killed by cervical dislocation and their spleens were removed in sterile conditions. The spleen was washed and reduced to pieces by using syringe needles. Spleen cells were then separated from the connective fibrous septa allowing the latter to sediment in a test tube for a few minutes under the same sterile hood. The spleen cells were resuspended into EMEM medium, washed by centrifugation (1500 rpm for 10') and resuspended into EMEM medium supplemented with penicillin and streptomycin.

Simultaneously, NS-1 myeloma cells were grown for 2 days in culture starting from an initial inoculum of approximately 500,000 cells. The cells were then washed in EMEM medium by centrifugation (1500 rpm for 10') and again resuspended into EMEM supplemented with penicillin and streptomycin.

The two cell pellets (one composed of spleen cells, the other of myeloma cells obtained through culture) were finally resuspended into 10 ml of EMEM medium, combined into a single test tube, and centrifuged for 10' at 1500 rpm, obtaining a pellet composed both of spleen cells and myeloma cell lines.

Immediately, within 1 minute, the cells were gently resuspended into 1 ml of fusion medium, to which 5 ml of EMEM medium were added over the following 3 minutes. During the subsequent 3 minutes, 7 ml of RPMI medium containing 20% complement-inhibited bovine fetal serum were added. The cells were centrifuged (1200 rpm for 15') and the pellet resuspended into 10 ml of HAT medium, to be then diluted into 200 ml of the same medium. After a 1 hour incubation at 36.5° C. in a controlled atmosphere room containing 5% $CO_2$, the cell suspension was dispensed into 10 96-well Microtiter plates (NUNC), 200 µl for each well, and incubated in the same room described above.

The plates containing the cells derived from the fusion were observed during the subsequent days to assess for a possible growth of hybridomas. In case of growth, the cell culture supernatant was evaluated for the presence of antibodies by ELISA. The hybridomas were then cloned by limiting dilution, expanded and, in part, maintained in liquid nitrogen.

Clones that by ELISA (following the described protocol) demonstrated a reactivity against Fab preparations obtained from HIV-seronegative patients' sera were immediately discarded. Clones that proved negative towards the preparations obtained from the seronegative patients' sera were assayed for their reactivity to the anti-gp120 IgG preparations purified from the seropositive patients. Clones positive for such reactivity were assayed in ELISA by using as the antigen the Fab fragments thereof, and employed in the immunization of mice (RB1Fabs). Mouse monoclonal antibodies capable of reacting against the latter preparation (RB1Fabs) were purified by using Montage PROSEP-A columns (Fisher) according to the manufacturer's directions. Finally, the purified and concentrated antibodies were evaluated for their ability to inhibit the binding of the anti-gp120-purified Fabs derived from the patients' serum (RB1Fabs) to the antigen itself (gp120) in an inhibition ELISA experiment, by modifying for mouse antibodies methods already described (Bugli et al, J. Virol. 2001), that is to say by using a preparation of peroxidase-conjugated goat polyclonal antibodies specifically directed towards the mouse Fab's conserved regions (Sigma, St. Louis, Mo.).

Two of the antibody clones that reacted against the purified human Fabs (RB1Fabs) were identified as also being able to inhibit the binding between purified Fabs (RB1Fabs) and gp120. Such clones were designated as Mab1 and Mab2.

For the preparation of the Fab fragments from the cultured cells, mRNA was extracted, cDNAs encoding for the light chain and the heavy chain portion that is a part of the Fab were amplified by described methods (CSH press, Phage display manual, ed. D. R. Burton, p. A1.10), and these cDNAs were then cloned together into an already described expression vector called RBCaf (Burioni et al, J. Imm. Meth, 1988). Briefly, the gene (amplified DNA) encoding for the heavy chain of each Fab was digested with the restriction enzymes XhoI and SpeI (Roche) for 1.5 hours at 37° C. and subsequently ligated into the cloning site of the vector for the heavy chains, digested in turn with the same enzymes. Instead, the light chains (amplified DNA) were digested with the enzymes SacI and XbaI (Roche) and then cloned into the similarly digested vector.

The recombinant constructs thus obtained for each of the 2 clones were then used to electro-transform *E. coli* XL1Blue strain (made competent through cold washes in glycerol), according to standardized protocols for the usage of 0.2 cm cuvettes (Voltage: 2500 V; Capacitance: 25 µF; Resistance: 200Ω).

ELISA Evaluation of Monoclonal Fabs Obtained through Cloning into RBCaf

Bacterium clones transformed with the RBCaf construct were inoculated into 10 ml of SB medium containing ampicillin and tetracycline at 501 g/ml and 10 µg/ml respectively, and grown with shaking at 37° C. until reaching an O.D.600=1. Successively, a specific inductor (IPTG-isopropylo-D-thiogalactopyranoside) was added at 1 mM final concentration, and the culture was kept shaking at 30° C. overnight. The cells were lysed by heat-shock (3 rounds of freezing-thawing at −80° C. and 37° C., respectively) and then centrifuged in order to separate the cell debris from the Fab-containing supernatant. The obtained soluble Fabs were assayed by ELISA. 96-well Microtiter plates (Nunc) were coated with the RB1 purified Fabs (300 ng per well) and BSA as the negative control antigen, and incubated overnight at 4° C. After removing the non-bound antigen, the plate was washed 5 times with PBS, and the non-specific binding sites were blocked with 3% albumin in PBS for 1 hour at 37° C. After removing the blocking solution, the cell culture supernatants treated as above and containing the soluble Fabs were added. This was followed by an incubation step at 37° C. for 2 hours. After a round of 10 washes with PBS/0.05% Tween 20, 40 µl of a 1:700 dilution in PBS/1% BSA of a polyclonal preparation of horseradish peroxidase-conjugated goat immunoglobulins (Sigma), directed against mouse Fabs, were added. After a 1 hour incubation at 37° C. and a further series of 10 washes, the substrate (OPD-o-phenylenediamine) was added to the wells. The plates were then incubated for 30 minutes at room temperature in the dark. The reaction was stopped with 1N sulphuric acid and the optical density was assessed by spectrophotometric reading at 450 nm.

At the end of the cloning, 40 recombinant bacterium clones were analyzed for each monoclonal antibody as just described and, for each of them, a clone capable of generating mouse Fabs able to bind the purified human Fabs (RB1Fabs) was selected. Successively, the light chain variable portion and heavy chain variable portion DNA sequences of these selected clones, designated as Pomona1 and Pomona2 (P1 and P2), were analyzed. Such sequences are those provided in the Sequence listing section.

Purification of the P1 and P2 Fabs

The P1 and P2 Fabs were then immunoaffinity purified, through columns filled with a G protein-containing (~2 mg/ml) sepharose resin, to which a polyclonal preparation of goat anti-mouse Fab antibodies (PIERCE, Ill.) was covalently bound. Briefly, a colony of each clone was inoculated into 10 ml of SB medium containing ampicillin and tetracycline at 50 µg/ml and 10 µg/ml, respectively. The culture, grown overnight at 37° C., was subinoculated into a flask with 500 ml of SB supplemented with the same concentration of antibiotics as before. The cells, subsequently induced with 1 mM IPTG, were kept shaking overnight at 30° C. The culture was centrifuged at 5000 rpm for 25 minutes and the pellet resuspended in PBS was sonicated. A subsequent centrifugation at 18,000 rpm for 25 minutes was needed to remove the cell debris and the supernatant was filtered and then slowly passed through the sepharose column as previously described. Then, the resin was washed with 10 volumes of PBS and finally the bound Fabs were eluted with an acid solution (elution buffer-$H_2O$/HCl pH 2.2) and the collected fractions were neutralised with the proper solution (Tris 1 M pH 9). The collected fractions were concentrated by ultrafiltration (Centricon, Millipore). The purity of the purified fraction was assessed by running an aliquot on a 12% sodium dodecyl sulphate/polyacrylamide gel (SDS-PAGE). Eventually, stepwise dilutions of such purified Fabs were assayed by ELISA as previously described. Monoclonal Fab preparations directed against the HCV E2 glycoprotein (e8; e20; e137; e509; Burioni et al, Hepatology, 1998) were included in each plate as negative controls.

The obtained results are disclosed in FIG. 1, wherein the mean optical density values (with their relative standard deviations) related to the monoclonal P1 and P2 Fabs are reported. All reported data were generated by ELISA experiments performed in 3 different sessions wherein each dilution point was repeated in duplicate.

These data show a high reactivity of both P1 and P2 Fabs towards the FabRB1 preparation, moreover such Fabs are not able to bind the panel of human Fabs characterized by a different binding specificity to FabRB1. Even at the highest concentration (~30 µg/ml) the two mouse Fabs, in fact, are not able to recognize the Fab preparations with different binding specificities; in fact, in all the experiments the O.D. 450 values resulted to be 0.5 or less, with respect to the higher than 2.5 values detected with the RB1 preparation. Furthermore, both the Fabs proved to be able to recognize the RB1 preparation even at the lowest concentration (~0.5 µg/ml) used in the experiments.

Evaluation of the Ability of the Obtained Anti-Idiotype Molecules to Stimulate a Specific Anti-gp120 Response in Animal Models The P1 and P2 molecules, obtained as described above, were used to immunize animal models other than mice, in order to assess their ability to stimulate a specific anti-HIV/gp120 response. Particularly, female 4-5 week old New Zealand rabbits (Allevamento Bettinardi, Novara, Italy), weighing between 2.3 and 2.5 kg, were used. The animals (6 per group) were divided into three cohorts:

A cohort: animals immunized with the anti-P1 idiotype Fab;
B cohort: animals immunized with the anti-P2 idiotype Fab;
C cohort: animals immunized with a control Fab (JO1) devoid of anti-idiotype features.

Two weeks before the beginning of the immunization protocol, up to a maximum of 5 ml of blood was drawn from each animal's ear medium artery in order to obtain pre-immune sera. 200 µg of each antigen, resuspended into 500 µl max. of physiological solution and 500 µl of adjuvant solution, were then administered at three week intervals by multiple injections (max. 10) on the back, after appropriate antiseptic preparation of the inoculum site. The purity of each immunoaffinity-purified antigen was assessed by SDS-PAGE. Moreover, prior to the emulsion with the adjuvant, each antigen solution was first filtrated through 0.2 µm filters. 2 weeks after the third immunization, a maximum of 5 ml of blood was drawn from each animal in order to evaluate the humoral response by ELISA. With an approach analogous to those disclosed in the previous paragraphs, ELISA plates were coated with 50 ng/well of gp120 (HIV IIIB) and kept overnight at 4° C. The following day, the unbound antigen was removed by washing with a physiological solution. The non-specific sites of each well were then blocked with a PBS/1% BSA solution, keeping the plates in incubation for 1 h at 37° C. Stepwise dilutions of the pre-immune and post-immune (after 3 immunizations) sera from each animal were then added to the wells and incubated for 1.5 hours at 37° C. The plates were then washed automatically 5 times with a PBS/0.05% Tween 20 solution, and the antibodies bound to the antigen were then detected with a suitable dilution of a horseradish peroxidase-conjugated anti-rabbit Ig polyclonal (Pierce). After a further hour incubation at 37° C., and another subsequent 5 washings, the obtained signal was read as previously described.

Figure 2:
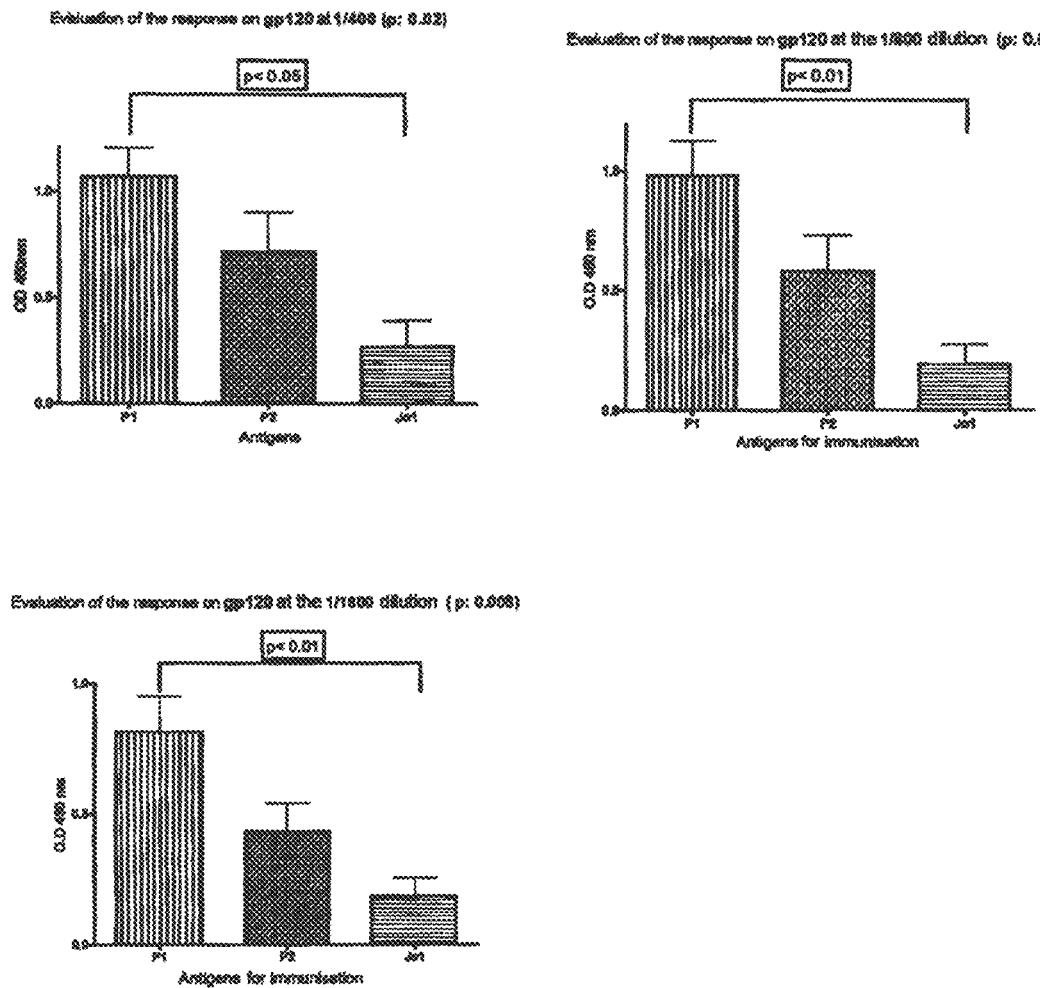

The obtained results are disclosed in FIG. 2, wherein the mean values (with their relevant standard deviations) of the anti-gp120 response stimulated into rabbits belonging to the 3 different immunization groups are reported. The reported data are related to ELISA experiments repeated in duplicate in three different sessions for each dilution point.

From this series of data it is evident that both the antibodies are able to evoke an anti-gp120 immune response in experimental animals, thereby turning out to be potentially useful molecules in vaccine applications. The response is also evident at high serum dilutions (1:1600), with a mean O.D. 450 nm increase above 1 in the case of animals immunized with P1, and of about 0.5 in the case of P2. The comparison between the data obtained from the cohorts immunized with the anti-idiotypes and those obtained from the cohort immunized with the mouse control antibody (JO-1) also allowed for verification of the statistical validity of the results. In particular, by applying a non-parametric test for non-paired data (Mann-Whitney test) to the study, it has been possible to demonstrate that the distribution of the results obtained from the 3 animal groups is not at all accidental, as evidenced by the p values below 0.05 in each case. Moreover, the significance increases at the highest serum dilutions ($\frac{1}{800}$ and $\frac{1}{1600}$), with p values below 0.01. Besides confirming the statistical validity of this experiment conducted on a minimal number of animals, the latter data testify the specificity of the observed phenomenon.

Immunization with gp120 of Rabbits Previously Immunized with Monoclonal Anti-Idiotype Antibodies Six weeks after the second boost with P1, P2, and JO1, rabbits respectively belonging to the A, B, and C cohorts were immunized with gp120. 200 µg of antigen resuspended into 500 µl of physiological solution and 500 µl of incomplete Freund's adjuvant (Gibco) were administered according to the same mode as previously described. Two weeks after the immunization, about 5 ml of blood were drawn from each animal in order to evaluate the anti-gp120 humoral response by ELISA, with an approach analogous to that previously described. The data were obtained by ELISA experiments repeated in duplicate for each dilution point and in three different sessions.

Figure 3:
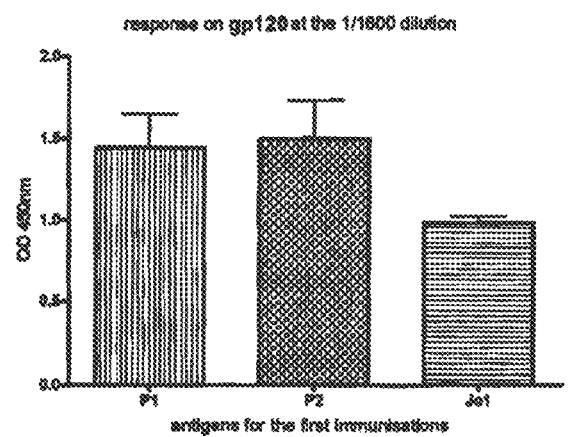
Figure 3:
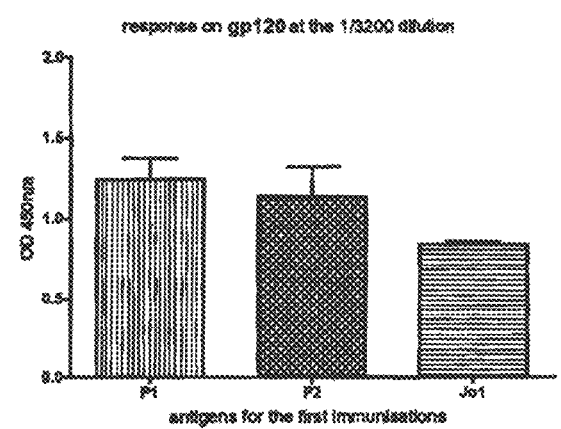

The data presented in FIG. 3, wherein the mean values (with their relevant standard deviations) of the anti-gp120 response stimulated into rabbits belonging to the 3 different immunization groups are reported, show that the 3 rabbit groups responded to gp120 after the first immunization and also point out the presence of a greater response in the rabbit cohorts immunized with P1 and P2 compared to the rabbit cohort immunized with JO1. These data indicate that animals exposed to P1 and P2 are able to mount a more effective immune response to gp120 compared to those exposed to a control antigen.

Evaluation of the Neutralising Activity of Sera from Rabbits Immunized with the Monoclonal Anti-Idiotype Antibodies The neutralisation experiment was performed by using U87.CD4 cells (CXCR4) (NIH AIDS Research & Reagent Program), an adherent-growing human glyoma cell line that expresses the CXCR4 co-receptor on its surface. The high glucose DMEM with Na-pyruvate and L-glutamine (Euro-Clone), supplemented with 300 µg/ml G418 (GIBCO), 1 µg/ml puromycin (Sigma), and 10% complement-inactivated bovine fetal serum (Euro-Clone), was used as the culture medium to maintain the cell line. The neutralising activity of the pre-immune serum, and of the serum collected after three immunizations with the anti-idiotype molecules (P1 and P2) or with the control antibody (JO1) was assessed for each animal. The BH8 isolate (GenBank # K02011), a virus belonging to the IIIB subtype, was used as the HIV-1 isolate.

First of all, the aforesaid cells were transferred to a 96-well microtiter plate (Costar), in order to have about $8 \times 10^3$ cells in each well. The next day, sterile transfer plates (Costar) were prepared wherein the virus was incubated with the sera to be tested. In particular, the culture medium containing the virus at a final load of 100 $TCID_{50}$, and a $\frac{1}{10}$ final dilution of each serum, after complement-inhibition at 56° C. for 30 minutes, were added to each well. A human polyclonal preparation derived from HIV-positive patients, which was known to be able to neutralise the HIV-1 isolate in question, was used as the positive control for the experiment. Instead, a preparation of standard immunoglobulins was used as the negative control. Each single point was repeated in triplicate, and kept in incubation in the transfer plates for 1 hour at 37° C. in a 5% $CO_2$ atmosphere. Thereafter, 100 µl of the solution containing the virus and the serum were transferred from the transfer plate to the infection plate that contained the cells, and kept in incubation overnight again at 37° C. in a 5% $CO_2$ atmosphere. In addition, a positive control for the infection, only containing cells and viruses (100 $TCID_{50}$), a control for the cell viability only containing cells, and a control for the toxicity only containing cells and serum, were inserted to complete the experiment and treated as described.

The following day, the infection plate was washed twice with sterile PBS, and 100 μl of the same culture medium as previously described were added to each well. The cells treated this way were then kept for six days at 37° C. in a 5% $CO_2$ atmosphere. At the end of the six days, the p24 produced was measured in the supernatant of each well with a commercial kit (Abbott AXSYM). The mean and the variability coefficient of the obtained p24 values were calculated for each serum tested in triplicate, which were then compared to the values obtained in the wells containing the infection positive control, tested in quintuplicate. This way it has been possible to evaluate the neutralising activity of each serum, expressed as the percentage of the decrease in the obtained p24 values compared to the control.

None of the pre-immune sera showed a neutralising activity, consistent with the data obtained on the sera collected after the immunizations with the mouse antibodies. Particularly, only the sera of animals immunized with the anti-idiotype molecules resulted in a decrease of the p24 measured levels. As for the P1 group, in fact, 3 out of 6 animals displayed a neutralising activity towards the HIV-1 isolate used, with percentages varying from a minimum of 31.5% to a maximum of 82.2%. Similar data were also obtained for two rabbits immunized with the P2 anti-idiotype, with neutralising values around 30%. The extent of the neutralising response and its presence in a considerable number of experimental animals makes it possible to hypothesize a profitable use of these molecules in diagnostic, and prophylactic and therapeutic vaccine practices. In confirmation of the specificity of the obtained results, it is important to note that, besides the aforementioned absence of neutralising activity in the pre-immune sera, none of the sera from animals immunized with the JO-1 control antibody showed a neutralising activity. The results obtained for each animal are summarized in the following table. The variability seen among the immunization % of animals immunized with the same antigen (P1 or P2) must not be surprising: it is simply due to the fact that each individual animal responds differently to the immunization.

| ANTIGEN | ANIMAL | % NEUTRALISATION BH8 |
|---------|--------|----------------------|
| P1 | 1 | 82.2 |
|  | 14 | 63.3 |
|  | 3 | 0 |
|  | 8 | 0 |
|  | 9 | 0 |
|  | 12 | 31.5 |
| P2 | 17 | 0 |
|  | 18 | 0 |
|  | 15 | 28 |
|  | 20 | 0 |
|  | 21 | 0 |
|  | 24 | 29.3 |
| JO1 | 10 | 0 |
|  | 16 | 0 |
|  | 4 | 0 |
|  | 7 | 0 |
|  | 5 | 0 |
|  | 22 | 0 |

Animals nos. 1, 14, 3, 8, 9, 12: immunized with P1
Animals nos. 17, 18, 15, 20, 21, 24: immunized with P2
Animals nos. 10, 16, 4, 7, 5, 22: immunized with JO1

REFERENCES

1. Bugli F, et al. J. Virol. 2001 October; 75(20):9986-90
2. Burioni R. Doctoral thesis, 1993
3. Carlos F. Barbas, et al. Phage display. Cold Spring Harbor Laboratory Press; New York (p. A10.10)
4. Hariharan K, et al. J. Virol. 1993 February; 67(2):953-60
5. Burioni R, et al. J. 1 mm. Methods 217:195-199 (1998)
6. Burioni R., et al. Hepatology 28:810-814 (1998)

---

The invention claimed is:

1. An anti-idiotype monoclonal antibody or a fragment thereof, comprising at least a variable portion of a light chain and a corresponding variable portion of a heavy chain, wherein the anti-idiotype monoclonal antibody or fragment thereof is capable of:

specifically reacting with an idiotype of human anti-gp120 antibodies, inhibiting binding between a gp120 antigen and human anti-gp120 antibodies, and evoking a neutralising anti-gp120 immune response in an animal, to which the anti-idotype monoclonal antibody or fragment thereof is administered, and wherein said variable portion of the light chain and corresponding variable portion of the heavy chain are selected to have the amino acid sequence identified as SEQ ID NO:2 and SEQ ID NO:1 respectively; or have the amino acid sequence identified as SEQ ID NO:4 and SEQ ID NO:3, respectively.

2. An anti-idiotype monoclonal antibody or a fragment thereof, comprising at least a variable portion of a light chain and a corresponding variable portion of a heavy chain, wherein the anti-idiotype monoclonal antibody or fragment thereof is capable of:

specifically reacting with an idiotype of human anti-gp120 antibodies, inhibiting binding between a gp120 antigen and human anti-gp120 antibodies, and evoking a neutralising anti-gp120 immune response in an animal, to which the anti-idotype monoclonal antibody or fragment thereof is administered, and wherein said variable portion of the light chain and corresponding variable portion of the heavy chain are selected to be encoded by the nucleic acid sequence identified as SEQ ID NO:6 and SEQ ID NO:5, respectively; or be encoded by the nucleic acid sequence identified as SEQ ID NO:8 and SEQ ID NO:7, respectively.

3. The anti-idiotype monoclonal antibody according to claim 1, wherein said anti-idiotype monoclonal antibody is a whole immunoglobulin.

4. The anti-idiotype monoclonal antibody according to claim 1, wherein said anti-idiotype monoclonal antibody is a Fab fragment.

5. The anti-idiotype monoclonal antibody according to claim 1, wherein said anti-idiotype monoclonal antibody is a single-chain antibody.

6. The anti-idiotype monoclonal antibody according to claim 1, wherein said anti-idiotype monoclonal antibody is conjugated to a carrier.

7. The anti-idiotype monoclonal antibody according to claim 1, wherein the animal is a human being.

8. An isolated amino acid sequence selected from the group consisting of SEQ ID NO:1, SEQ ID NO:2, SEQ ID NO:3 and SEQ ID NO:4.

9. An immunogenic composition comprising an immunologically effective amount of at least one neutralising anti-idiotypic monoclonal antibody according to claim 1 and a pharmaceutically acceptable carrier, diluent and/or adjuvant.

10. A kit for detection of human immunodeficiency virus (HIV), comprising the following components: a first container comprising the anti-idiotype monoclonal antibody according to claim 1; and a second container comprising an HIV gp120 antigen.

11. A method for manufacturing a composition comprising the anti-idiotypic monoclonal antibody according to claim 1, the method comprising mixing the anti-idiotypic monoclonal antibody according to claim 1 with an acceptable carrier, diluent and/or adjuvant.

12. A method for detection of anti-human immunodeficiency virus (HIV) gp 120 antibodies or antibody subpopulations in a biological sample, the method comprising obtaining the biological sample from a subject, contacting the biological sample with the anti-idiotype monoclonal antibody of claim 1 for a time and under condition to allow binding of the anti-idiotypic antibody binding to anti-gp120 antibodies present in the biological sample to form an anti-idiotypic antibody-anti-gp120 antibody immune complex, and detecting the anti-idiotypic antibody-anti-gp120 antibody immune complex.

13. The method of claim 12, wherein the subject is a human being.

* * * * *

SEQUENCE LISTING

<160> NUMBER OF SEQ ID NOS: 8

<210> SEQ ID NO 1
<211> LENGTH: 129
<212> TYPE: PRT
<213> ORGANISM: Mus musculus

<400> SEQUENCE: 1

Glu Leu Val Lys Pro Gly Ala Ser Val Lys Ile Ser Cys Lys Ala Ser
1               5                   10                  15

Gly Tyr Ser Phe Thr Asp Tyr Asn Met Asn Trp Val Lys Gln Ser Asn
            20                  25                  30

Gly Lys Ser Leu Glu Trp Ile Gly Val Ile Asn Pro Asn Ser Gly Thr
        35                  40                  45

Thr Gly Tyr Asn Gln Lys Phe Lys Gly Lys Ala Thr Leu Thr Val Asp
    50                  55                  60

Gln Ser Ser Ser Thr Ala Tyr Met Gln Leu Asn Ser Leu Thr Ser Glu
65                  70                  75                  80

Asp Ser Ala Val Tyr Tyr Cys Ala Glu Tyr Tyr Gly Glu Asp Pro
                85                  90                  95

-continued

```
Phe Ala Tyr Trp Gly Gln Gly Thr Leu Val Thr Val Ser Thr Ala Lys
                100                 105                 110

Thr Thr Pro Pro Ser Val Tyr Pro Leu Ala Pro Gly Ser Ala Ala Gln
        115                 120                 125

Thr

<210> SEQ ID NO 2
<211> LENGTH: 102
<212> TYPE: PRT
<213> ORGANISM: Mus musculus

<400> SEQUENCE: 2

Ser Leu Ala Val Ser Leu Gly Gln Arg Ala Thr Ile Ser Cys Arg Ala
1               5                   10                  15

Ser Gln Ser Val Ser Thr Ser Ser Tyr Ser Tyr Met His Trp Tyr Gln
            20                  25                  30

Gln Lys Pro Gly Gln Pro Pro Lys Leu Leu Ile Lys Tyr Ala Ser Asn
        35                  40                  45

Leu Glu Ser Gly Val Pro Ala Arg Phe Ser Gly Ser Gly Ser Gly Thr
    50                  55                  60

Asp Phe Thr Leu Asn Ile His Pro Val Glu Glu Glu Asp Thr Ala Thr
65                  70                  75                  80

Tyr Tyr Cys Gln His Ser Trp Glu Ile Pro Tyr Thr Phe Gly Gly Gly
                85                  90                  95

Thr Lys Leu Glu Ile Lys
            100

<210> SEQ ID NO 3
<211> LENGTH: 131
<212> TYPE: PRT
<213> ORGANISM: Mus musculus

<400> SEQUENCE: 3

Leu Val Gln Pro Gly Gly Ser Leu Lys Leu Ser Cys Ala Ala Ser Gly
1               5                   10                  15

Ile Asp Phe Ser Arg Phe Trp Met Ser Trp Ile Arg Arg Ala Pro Gly
            20                  25                  30

Lys Gly Leu Glu Trp Ile Gly Glu Ile Asp Pro Asp Gly Ser Thr Ile
        35                  40                  45

Asn Tyr Ala Pro Ser Leu Lys Asp Lys Phe Ile Ile Ser Arg Asp Asn
    50                  55                  60

Ala Lys Asn Thr Leu Tyr Leu Gln Met Ser Lys Val Arg Ser Glu Asp
65                  70                  75                  80

Thr Ala Leu Tyr Tyr Cys Ala Arg Glu Gly Ala Tyr Gly Asn Tyr Asp
                85                  90                  95

Cys Ala Met Asp Tyr Trp Gly Gln Gly Thr Ser Val Thr Val Ser Ser
                100                 105                 110

Ala Lys Thr Thr Pro Pro Ser Val Tyr Pro Leu Ala Pro Gly Ser Ala
        115                 120                 125

Ala Gln Thr
        130

<210> SEQ ID NO 4
<211> LENGTH: 103
<212> TYPE: PRT
<213> ORGANISM: Mus musculus
```

-continued

<400> SEQUENCE: 4

Ser Leu Pro Val Ser Leu Gly Asp Gln Ala Ser Ile Ser Cys Arg Ser
1               5                   10                  15

Ser Gln Asn Ile Val His Ser Asn Gly Asn Thr Tyr Leu Glu Trp Tyr
            20                  25                  30

Leu Gln Arg Pro Gly Gln Ser Pro Lys Leu Leu Ile Tyr Met Val Ser
        35                  40                  45

Asn Arg Phe Ser Gly Val Pro Asp Arg Phe Ser Gly Ser Gly Ser Gly
    50                  55                  60

Thr Asp Phe Thr Leu Lys Ile Ser Arg Val Glu Ala Glu Asp Leu Gly
65                  70                  75                  80

Val Tyr Tyr Cys Phe Gln Gly Ser His Ala Pro Pro Thr Phe Gly Gly
                85                  90                  95

Gly Thr Lys Leu Glu Ile Lys
            100

<210> SEQ ID NO 5
<211> LENGTH: 387
<212> TYPE: DNA
<213> ORGANISM: Mus musculus

<400> SEQUENCE: 5
gagctggtga agcctggcgc ttcagtgaag atatcctgca aggcttctgg ttactcattc      60
actgactaca acatgaactg ggtgaagcag agcaatggaa agagccttga gtggattgga     120
gtaattaatc ctaactctgg tactactggc tacaatcaga agttcaaggg caaggccaca     180
ttgactgtag accaatcttc cagcacagcc tacatgcagc tcaacagcct gacatctgag     240
gactctgcag tctattactg tgcagaatat tactacggcg aggatccttt tgcttactgg     300
ggccaaggga ctctggtcac tgtctctaca gccaaaacga cacccccatc tgtctatcca     360
ctggcccctg gatctgctgc ccaaact                                          387

<210> SEQ ID NO 6
<211> LENGTH: 306
<212> TYPE: DNA
<213> ORGANISM: Mus musculus

<400> SEQUENCE: 6
tccttagctg tatctctggg gcagagggcc accatctcat gcagggccag ccaaagtgtc      60
agtacatcta gctatagtta tatgcactgg taccaacaga aaccaggaca gccacccaaa     120
ctcctcatca gtatgcatc caacctagaa tctggggtcc ctgccaggtt cagtggcagt     180
gggtctggga cagacttcac cctcaacatc catcctgtgg aggaggagga tactgcaaca     240
tattactgtc agcacagttg ggagattccg tacacgttcg gaggggggac caagctggaa     300
ataaaa                                                                 306

<210> SEQ ID NO 7
<211> LENGTH: 393
<212> TYPE: DNA
<213> ORGANISM: Mus musculus

<400> SEQUENCE: 7
ctggtgcagc ctggaggatc cctgaaactc tcctgtgcag cctcaggaat tgattttagt      60
agattctgga tgagttggat tcggcgggct ccagggaaag gactagaatg gattggagaa     120
attgatccag atgcagtac aataaactat gcaccatctc taaggataa attcatcatc     180 tccagagaca acgccaaaaa tacgctgtac ctgcaaatga gcaaagtgag atctgaggac     240

-continued

```
acagcccttt attactgtgc aagagagggg gcctatggta actatgactg tgctatggac    300
tactggggtc aaggaacctc agtcaccgtc tcctcagcca aaacgacacc cccatctgtc    360
tatccactgg cccctggatc tgctgcccaa act                                 393

<210> SEQ ID NO 8
<211> LENGTH: 309
<212> TYPE: DNA
<213> ORGANISM: Mus musculus

<400> SEQUENCE: 8
tccctgcctg tcagtcttgg agatcaagcc tccatctctt gcagatctag tcagaacatt     60
gtacatagta atggaaacac ctatttagaa tggtacctgc agaggccagg ccagtctcca    120
aagctcctga tctacatggt ttccaatcga ttttctgggg tcccagacag gttcagtggc    180
agtggatcag ggacagattt cacactcaag atcagcagag tggaggctga ggatctagga    240
gtttattact gctttcaagg ttcacatgct cctccgacgt tcggtggagg caccaagctg    300
gaaatcaaa                                                            309
```